US007618587B2

(12) United States Patent
Kawate

(10) Patent No.: US 7,618,587 B2
(45) Date of Patent: Nov. 17, 2009

(54) ANALYZERS AND METHODS OF ANALYZING BLOOD

(75) Inventor: Yasunori Kawate, Kakogawa (JP)

(73) Assignee: Sysmex Corporation, Kobe-shi (JP)

(*) Notice: Subject to any disclaimer, the term of this patent is extended or adjusted under 35 U.S.C. 154(b) by 481 days.

(21) Appl. No.: 10/629,296

(22) Filed: Jul. 28, 2003

(65) Prior Publication Data
US 2004/0018629 A1 Jan. 29, 2004

(30) Foreign Application Priority Data
Jul. 29, 2002 (JP) ............................. 2002-219187
Jun. 30, 2003 (JP) ............................. 2003-188895

(51) Int. Cl.
G01N 21/66 (2006.01)

(52) U.S. Cl. .................... 422/73; 422/50; 422/55; 422/67; 422/68.1; 422/82.05; 422/82.08; 422/82.09; 422/119; 435/7.1; 435/7.21; 435/7.25; 435/287.2; 436/518; 436/523; 436/524; 436/528; 436/10; 436/164; 436/165; 436/172

(58) Field of Classification Search ........... 422/50, 422/55, 67, 73, 68.1, 82.05, 99, 108, 119, 422/105, 187–189, 82.08, 82.09; 435/7.1, 435/7.2, 7.21, 7.25, 7.8, 287.2, 962; 436/63, 436/164, 172, 523–529, 531–534, 514, 536, 436/538, 10, 16, 165, 175, 518
See application file for complete search history.

(56) References Cited
U.S. PATENT DOCUMENTS
4,284,412 A 8/1981 Hansen et al.
6,106,778 A * 8/2000 Oku et al. .................. 422/50
6,228,652 B1 * 5/2001 Rodriguez et al. .......... 436/63
6,287,791 B1 9/2001 Terstappen et al.
7,390,677 B2 * 6/2008 Nakashima et al. ........ 436/533

FOREIGN PATENT DOCUMENTS
EP 0 347 210 A2 12/1989
EP 0 455 125 A2 11/1991
EP 0 722 087 A1 7/1996
JP B-19349 * 11/1983
JP H6-19349 3/1994
JP 11-101798 4/1999
WO WO 92/09682 A1 6/1992
WO WO 02/23154 A2 3/2002

OTHER PUBLICATIONS
Ruzicka, MD, K.; Veitl, MD, M.; Thalhammer-Scherrer, MD, R.; Schwarzinger, MD, I., "The New Hematology Analyzer Sysmex XE-2100: Performance Evaluation of a Novel White Blood Cell Differential Technology", Arch Pathol Lab Med, Mar. 2001, vol. 125, pp. 391-396.

* cited by examiner

Primary Examiner—Gailene R Gabel
(74) Attorney, Agent, or Firm—Brinks Hofer Gilson & Lione

(57) ABSTRACT

Analyzers and methods of analysis are described for performing blood cell counting and immunoassay on a whole blood specimen in one measurement section. An assay sample is prepared by blending carrier particles sensitized with an antibody or an antigen against a substance to be immunoassayed and a fluorescent dye for staining blood cells with the whole blood specimen. Optical information is detected from a particle in the assay sample, and the blood cells are differentiated and counted based on the detected optical information. A rate of agglutination of the carrier particles is obtained based on the detected optical information, thereby enabling detection of the substance to be immunoassayed.

12 Claims, 13 Drawing Sheets

ANALYZERS AND METHODS OF ANALYZING BLOOD

RELATED APPLICATIONS

This application claims priority under 35 U.S.C. § 119 to Japanese Patent Application Nos. 2002-219187, filed Jul. 29, 2002, and 2003-188895, filed Jun. 30, 2003.

FIELD OF THE INVENTION

The present invention relates to blood analyzers and analysis methods for efficiently performing blood cell counting and immunoassay on a specimen.

BACKGROUND

In the field of laboratory tests, various analysis apparatuses such as blood cell counters, immunoassay apparatuses, blood coagulation analyzers, and biochemical analyzers are used depending on the desired measurement parameters. Thus, it is typically necessary to manage multiple analysis apparatuses. Moreover, it is typically necessary to collect multiple specimens from a patient depending on the parameters to be measured, which places a considerable burden on the patient. Consequently, an automated analyzer capable of analyzing multiple parameters in a single specimen would be desirable.

Blood cell counting involves differentiating blood cells contained in blood (i.e., whole blood) and counting according to blood cell type. The blood cells are generally differentiated into erythrocytes, leukocytes, platelets, and the like. Thus, erythrocyte number, leukocyte number, and platelet number are representative parameters of blood cell counting. In addition, reticulocytes which emerge in peripheral blood in an immature state of erythrocytes are differentiated and counted in some cases.

An analysis apparatus for blood cell counting includes an automated hematology analyzer, such as the XE-2100 supplied by Sysmex Corporation. Here, blood cells are stained with specific fluorescent dyes, optical information (e.g., forward scattered light, side scattered light and fluorescence) is detected from the respective blood cells by flow cytometry, and the blood cells are differentiated and counted by combining this optical information. In addition, this analysis apparatus has a counting function for reticulocytes, whereby forward scattered light intensity and side fluorescence intensity are detected from the fluorescently stained blood cells by reacting with staining solution without hemolysis. Two dimensional scattergrams are made using these as parameters to differentiate the blood cells into platelets, erythrocytes, reticulocytes and the like. The staining solution for fluorescent staining of the blood cells contains a dye which stains nucleic acid contained in the blood cells, and stains the leukocytes and reticulocytes. The side fluorescence intensity detected from the blood cells provides information indicative of the amount of nucleic acid in the blood cells, and the blood cells can be differentiated by combining the forward scattered light intensity (size information) and the side fluorescence intensity (nucleic acid amount information).

In addition to blood cell number, mean corpuscular volume (MCV) and hematocrit value are also used as parameters of blood cell counting. MCV is a mean value of erythrocyte sizes in whole blood. The hematocrit value is a percentage of blood cell component occupying the whole blood. Since an erythrocyte volume occupies a vast majority of the blood cell volume, the hematocrit value is calculated by measuring the erythrocyte number and MCV in the whole blood, multiplying the MCV by the erythrocyte number in the whole blood, and dividing it by the volume of the whole blood.

An immunoassay is an assay method for making an antigen or an antibody contained in a specimen (e.g., blood) a substance to be assayed, which is detected by taking advantage of an antigen antibody reaction. Representative immunoassays include an enzyme immunoassay (EIA) method, a radioimmunoassay (RIA) method, a particle agglutination method, and the like. The particle agglutination method is a method in which a substance to be immunoassayed is detected by blending carrier particles sensitized with an antibody or an antigen corresponding to the substance to be assayed with a sample, inducing a particle agglutination reaction due to the antigen antibody reaction, and measuring the degree of the particle agglutination (degree of agglutination) from changes in absorbance and light scatter.

In conventional particle agglutination methods, a sample containing carrier particles after the agglutination reaction is measured by flow cytometry and the degree of agglutination is obtained based on optical information obtained from the respective particles. When the information which reflects size of the carrier particles (e.g., forward scattered light) is used as the optical information, unagglutinated carrier particles can be discriminated from agglutinated carrier particles, and the degree of agglutination of the carrier particles can be obtained. A rate of agglutination method for determining degree of agglutination is described in JP-B-6-19349. In this method, scattered light intensities of respective particles are measured by a flow cytometer. Non-agglutinated single particles and agglutinated particles which occur by agglutinating multiple carrier particles are differentiated according to their respective scattered light intensities. Single particle number (M) and agglutinated particle number (P) are counted to obtain a total particle number (T) which is a sum of M and P, and P/T is calculated as the rate of agglutination. Since the reaction can be caught at a stage where two carrier particles are agglutinated, an extremely high sensitivity immunoassay becomes possible. In this rate of agglutination assay, various methods (e.g., in which the rate of agglutinated particles measured equals or exceeds a certain number) can be used depending on the assay level range of the substance to be immunoassayed. The rate of agglutination assay method in the above-described JP-B-6-19349 is used for the immuno-agglutination assay apparatus PAMIA series supplied by Sysmex Corporation.

Whole blood, serum, plasma, and the like are used as samples in the above-described apparatuses for blood cell counting and immunoassay. However, while whole blood samples are typically used in the blood cell counter, serum or plasma are typically used in other apparatuses (e.g., the immunoassay apparatuses). A blood cell counting/immunoassay apparatus using whole blood in which blood cell counting and immunoassay can both be carried out is described in U.S. Pat. No. 6,106,778. This apparatus has a blood cell counting portion and an immunoassay portion, and measures by dispensing the whole blood sample into the blood cell counting portion and the immunoassay portion, respectively. In the immunoassay portion, the immunoassay is carried out by hemolysing the whole blood sample with a hemolytic agent and using latex reagents.

However, when both blood cell counting and immunoassay are to be performed, it would be highly desirable that the blood cell counting and the immunoassay be carried out in an identical measurement section in order to reduce the amount of specimen collected from a patient and to enable measurement by a single small analyzer.

SUMMARY OF THE INVENTION

The scope of the present invention is defined solely by the appended claims, and is not affected to any degree by the statements within this summary.

A first analyzer embodying features of the present invention includes (a) a sample preparing portion configured for preparing an assay sample, wherein the assay sample contains at least one reagent and a blood specimen; (b) a light source for irradiating the assay sample; (c) a light detector for detecting optical information from a particle in the assay sample; and (d) an analyzing portion where blood cell counting and detection of a substance to be immunoassayed are carried out based on the optical information detected by the light detector.

A second analyzer embodying features of the present invention includes (a) a sample preparing portion, which is configured for preparing a sample for an immunoassay by adding a reagent for the immunoassay to one of at least two split blood specimens, and for preparing a sample for blood cell counting by adding a reagent for the blood cell counting to another of the at least two split blood specimens; (b) a light source for irradiating the sample for immunoassay and the sample for blood cell counting; (c) a light detector for detecting optical information from a particle in each of the sample for immunoassay and the sample for blood cell counting; and (d) an analyzing portion, wherein a substance to be immunoassayed is detected based on the optical information detected from the particle in the sample for immunoassay, and wherein the blood cell counting is performed based on the optical information detected from the particle in the sample for blood cell counting.

A third analyzer embodying features of the present invention includes (a) a sample preparing portion configured for preparing an assay sample by blending carrier particles sensitized with an antibody or an antigen against a substance to be immunoassayed and a fluorescent dye for staining blood cells with a blood specimen; (b) a light detecting portion containing a flow cell for flowing the assay sample, a light source for irradiating the assay sample flowing through the flow cell, and a detector for detecting forward scattered light and fluorescence emitted from a particle in the assay sample; and (c) an analyzing portion, wherein blood cell count and detection of the substance to be immunoassayed are performed based on the forward scattered light and the fluorescence detected by the light detecting portion.

A fourth analyzer embodying features of the present invention includes (a) a sample preparing portion configured for preparing an assay sample by adding at least one reagent to a blood specimen; a detecting portion for detecting a physical property of a particle in the assay sample; and an analyzing portion for performing blood cell counting and detection of a substance to be immunoassayed based on the physical property detected by the detecting portion.

A first method of analyzing blood embodying features of the present invention includes (a) preparing an assay sample by adding at least one reagent to a blood specimen; (b) irradiating the assay sample; (c) detecting optical information from a particle in the assay sample; and (d) performing blood cell counting and detection of a substance to be immunoassayed based on the optical information detected.

A second method of analyzing blood embodying features of the present invention includes (a) preparing a sample for an immunoassay by adding a reagent for the immunoassay to one of at least two split blood specimens; (b) preparing a sample for blood cell counting by adding a reagent for the blood cell counting to another of the at least two split blood specimens; (c) irradiating the sample for the immunoassay and detecting optical information from a particle in the sample for the immunoassay; (d) irradiating the sample for blood cell counting and detecting optical information from a particle in the sample for blood cell counting; (e) detecting a substance to be immunoassayed based on optical information from the particle in the sample for the immunoassay; and (f) performing blood cell counting based on the optical information from the particle in the sample for blood cell counting.

DETAILED DESCRIPTION

Blood analyzers embodying features of the present invention and methods for their use in assays are described below. In blood analyzers embodying features of the present invention, blood cell counting and immunoassay by the particle agglutination method are simultaneously performed for an identical sample. Using the flow cytometry method, forward scattered light and side fluorescence are detected as optical information reflecting characteristics of the respective particles from the sample containing blood cells and carrier particles. A two dimensional scattergram is made using this optical information as parameters. Plots corresponding to respective particles that emerged on the two dimensional scattergram are differentiated by type of blood cell and carrier particles depending on their emergence locations, and counted. For the carrier particles, a degree of agglutination is obtained based on the optical information detected.

Figure 1:
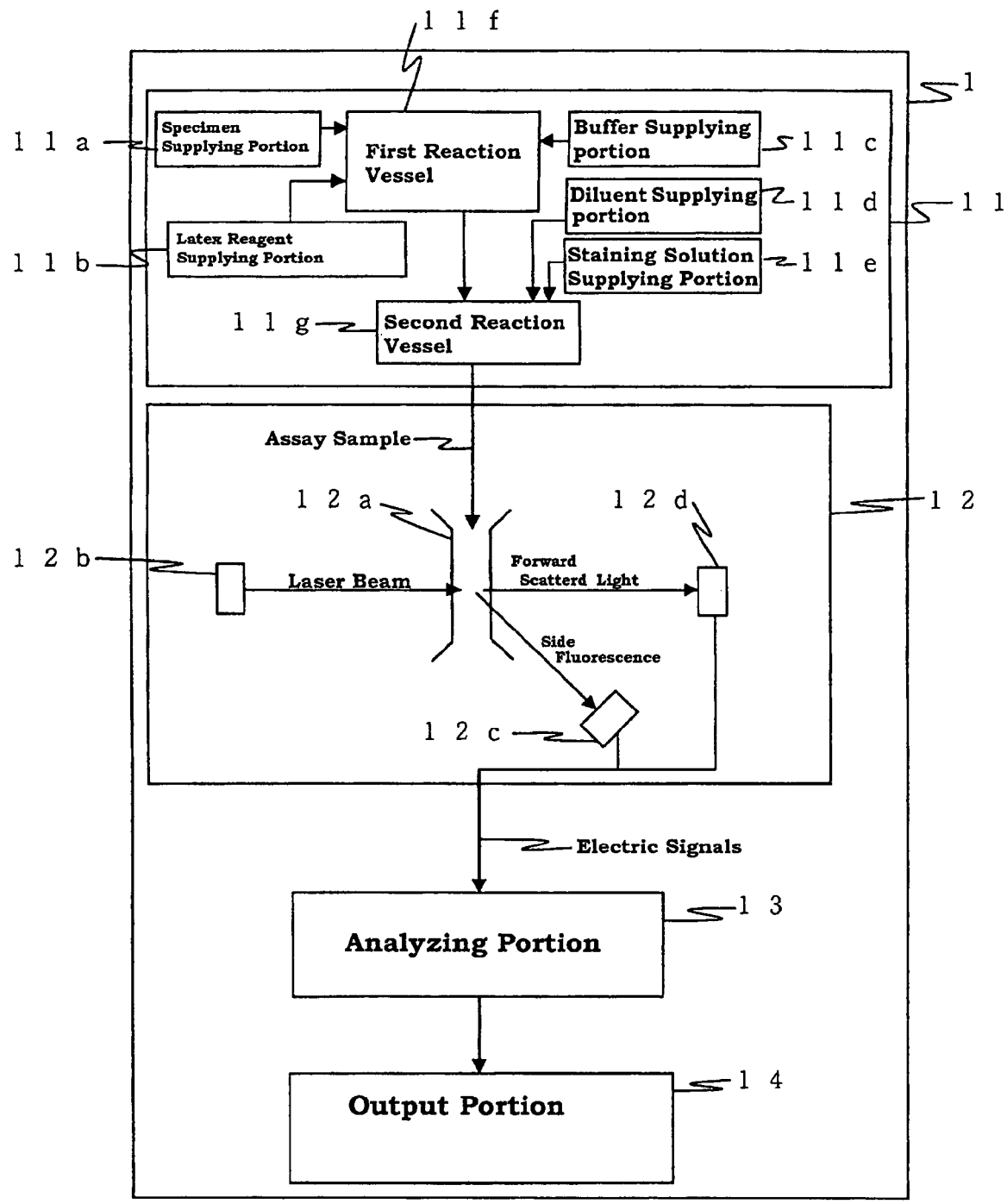
FIG. 1 is a scheme illustrating a configuration of a first blood analyzer embodying features of the present invention.

FIG. 1 is a figure showing a configuration of a blood analyzer embodying features of the present invention. The blood analyzer 1 includes a sample preparing portion 11, a light detecting portion 12, an analyzing portion 13 and an output portion 14.

The sample preparing portion 11 is for preparing an assay sample by adding given reagents (e.g., carrier particles, a diluent, a staining solution) to a specimen and reacting them therewith. In the sample preparing portion 11, the blood cells in the specimen are fluorescently stained. Carrier particles sensitized with an antibody or an antigen corresponding to a substance to be immunoassayed are added in order to perform a particle agglutination reaction. As carrier particles, it is possible to use particles typically used for the particle agglutination method, for example, latex particles, magnetic particles, glass particles, dendrimers, and the like, and combinations thereof. As the antigen or antibody which sensitizes the carrier particles when the substance to be immunoassayed is an antibody, an antigen which performs an antigen antibody reaction specific for the antibody maybe used. When the substance to be immunoassayed is an antigen, then an antibody which performs an antigen antibody reaction specific to the antigen may be used. For example, when the assay parameter is CEA antigen (carcinoembryonic antigen), anti-CEA antibody is sensitized. When the assay parameter is anti-HBs antibody, HBs antigen is sensitized.

The assay sample prepared at the sample preparing portion 11 is delivered in solution to the light detecting portion 12. The light detecting portion 12 is for detecting side fluorescence and forward scattered light from the particles in the sample by flow cytometry. The assay sample prepared at the sample preparing portion 11 is flowed into a flow cell 12a of the light detecting portion 12 and forms a sample flow. A laser beam is emitted from a laser beam source 12b, and the sample flow at the flowcell 12a is irradiated. Then, the side fluorescence generated when the particle in the sample flow cuts across a laser beam emitted area is received by a photo multiplier tube 12c and photoelectrically transferred to electric signals. The forward scattered light generated when the particle in the sample flow cuts across a laser beam emitted area is received by a photo diode 12d and photoelectrically transferred to electric signals.

The electric signals of the side fluorescence and the forward scattered light detected by the light detecting portion 12 are delivered to the analyzing portion 13. The analyzing portion 13 includes a computer made up of a hard disc, CPU, ROM, RAM, and on the like. At the analyzing portion 13, side fluorescence intensity and forward scattered light intensity are obtained by signals of each particle. Then, a two dimensional scattergram is made using the side fluorescence intensity and the forward scattered light intensity as parameters. The particles that emerged on the two dimensional scattergram are differentiated into various blood cells and carrier particles depending on their emergence locations, and counted.

Since the forward scattered light intensity reflects the size of a particle, the particles can be differentiated using only the forward scattered light intensity when the sizes differ by particle type. Among blood cells (e.g., platelets, erythrocytes and leukocytes), the platelet is the smallest and the leukocyte is the largest. However, the sizes of these blood cells are not definitely defined, and since the sizes overlap for different types of cells, it is difficult to precisely differentiate based only on size information of the forward scattered light intensity. Thus, the side fluorescence intensity is detected as the optical information reflecting characteristics other than the size of each particle. When fluorescent staining was previously achieved with a dye that stains nucleic acid contained in the blood cell, the side fluorescence intensity detected from the blood cell becomes the information that reflects amount of the nucleic acid in the blood cell. The blood cells can be differentiated more precisely by combining the forward scattered light intensity (size information) and the side fluorescence intensity (nucleic acid amount information).

To simultaneously perform blood cell counting and immunoassay, the carrier particles used for the immunoassay are such that the emergence locations of the particles do not overlap with those of the blood cells on the two dimensional scattergram. For example, the forward scattered light intensity is controlled by altering the sizes of the carrier particles. In addition, the side fluorescence intensity is controlled by including a fluorescent dye in the carrier particle or by altering a concentration of the fluorescent dye. Thus, if the carrier particles emerge at locations different from those of the blood cells on the two dimensional scattergram, it becomes possible to differentiate the blood cells and the carrier particles. When particles that are much smaller or larger than the blood cells are used as the carrier particles, it is possible to differentiate the particles in the sample into carrier particles and blood cells by difference in forward scattered light intensity. When carrier particles that are similar in size than the blood cells are used, the carrier particles and the blood cells can be differentiated by combining the forward scattered light intensity and the fluorescence intensity.

For carrier particles differentiated from blood cells on the two dimensional scattergram, the degree of agglutination is obtained and the substance to be immunoassayed is detected. The rate of agglutination described in JP-B-6-19349 is used as the degree of agglutination based on the forward scattered light intensity of the carrier particles. This rate of agglutination is calculated as follows. First, the scattered light intensity of each particle is obtained by flow cytometry. The particles are then differentiated into non-agglutinated single particles and agglutinated particles formed by agglutinating multiple carrier particles according to the respective scatter intensities. A single particle number (M) and an agglutinated particle number (P) are counted, a total particle number (T) which is a sum of M and P is obtained, and P/T is calculated as the rate of agglutination.

The rate of agglutination of the carrier particles is converted into a concentration of the substance to be immunoassayed based on a standard curve previously prepared by measuring specimens containing the substance to be immunoassayed at known concentrations. Thus, the concentration of the substance to be immunoassayed in the unknown specimens is obtained.

Figure 2:
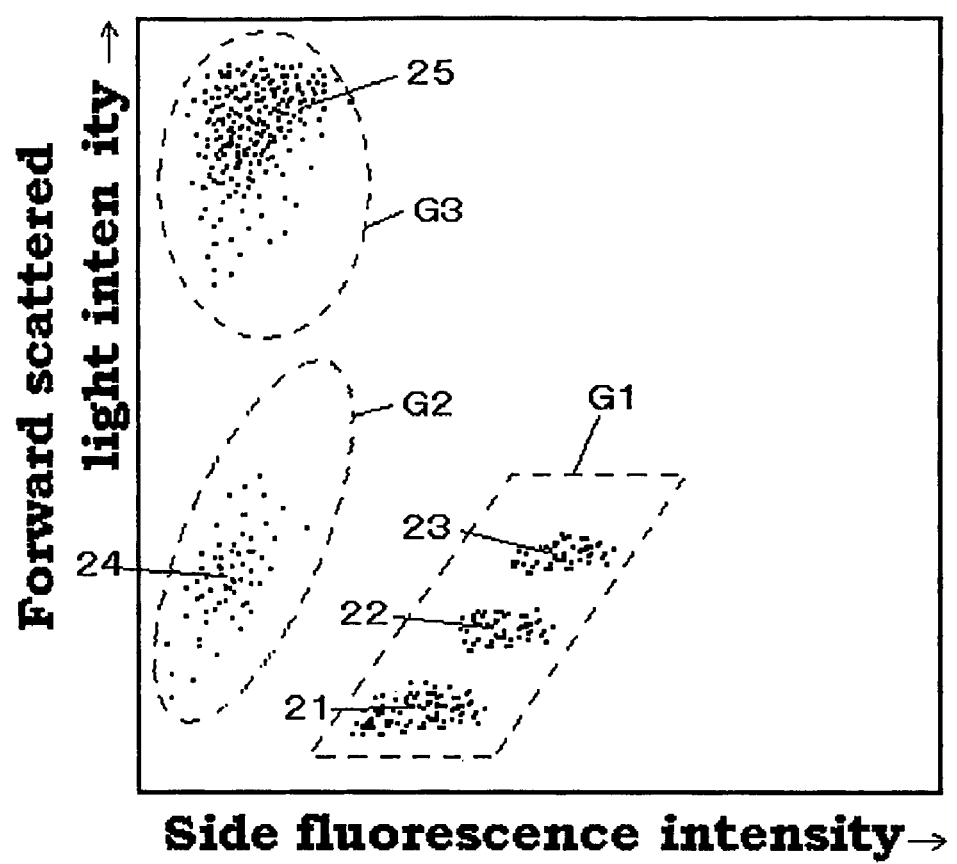
FIG. 2 is a plot illustrating carrier particles and blood cells that emerged at different locations on a two dimensional scattergram.

An example of a two dimensional scattergram from an assay with a blood analyzer embodying features of the present invention is shown in FIG. 2. This figure is a two dimensional scattergram made on the basis of the forward scattered light and the side fluorescence detected from a sample prepared by mixing fluorescent latex particles containing a fluorescent dye as the carrier particles and a given fluorescent dye for staining the blood cells with a whole blood specimen. The vertical and horizontal axes represent the forward scattered light intensity and the side fluorescence intensity, respectively. The carrier particles emerge segregated into separate populations because the forward scattered light intensity differs depending on patterns of agglutination, such as unagglutinated single particles 21, agglutinated double particles which occur by agglutinating two carrier particles 22, and agglutinated triple particles 23 which occur by agglutinating three carrier particles. As the blood cells, platelets 24 and erythrocytes 25 emerge, they may be differentiated from the carrier particles by the difference in forward scattered light intensity and side fluorescence intensity.

Figure 3:
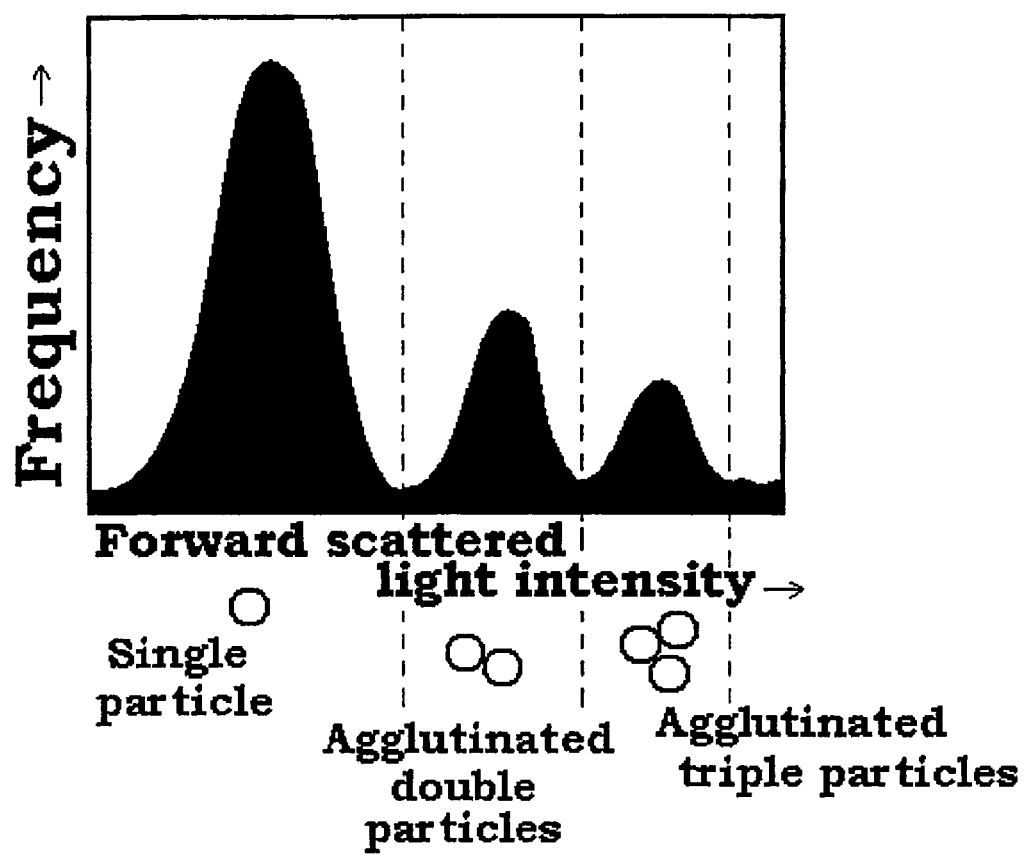
FIG. 3 is a histogram of particles that emerged in an area of the carrier particles on the two dimensional scattergram.

In FIG. 2, G1 is determined beforehand as the area where the carrier particles emerge. An example of particle size distribution of the carrier particles which emerge in the area G1 is shown in the histogram of FIG. 3. The vertical and horizontal axes represent the particle number (frequency) and the forward scattered light intensity, respectively. The agglutinated particles and the single particles are differentiated by determining a threshold for the forward scattered light intensity.

An antigen (antibody) concentration of each immunoassay parameter can be obtained by deriving the total particle number T from the particle number M of the differentiated single particles and the particle number P of the agglutinated particles (P is the sum of agglutinated particles equal to or greater than 2), calculating the rate of agglutination P/T, and performing the concentration conversion based on the standard curve previously prepared.

The blood cells emerge on the two dimensional scattergram making populations according to the difference in forward scattered light intensity and side fluorescence intensity. Thus, the blood cells are counted by previously determining the area specific for each type of blood cell and counting the particle number in each area. In FIG. 2, the areas G2 and G3 are for differentiating the platelets and the erythrocytes, respectively.

If the emergence locations of the carrier particles and the blood cells are made different on the two dimensional scattergram by appropriately controlling the particle diameters of the carrier particles and the fluorescent dye concentrations contained in the carrier particles or the concentrations of the fluorescent dye for staining the blood cells, then the blood cells and the carrier particles can be definitely differentiated. In addition, when the immunoassay is carried out with multiple parameters, the first carrier particles sensitized with the antibody or antigen corresponding to the first assay parameter and the second carrier particles sensitized with the antibody or antigen corresponding to the second assay parameter can be prepared. At that time, the first and second particles can be differentiated on the two dimensional scattergram by altering the concentrations of the fluorescent dyes contained in the first and second carrier particles, respectively.

Figure 4:
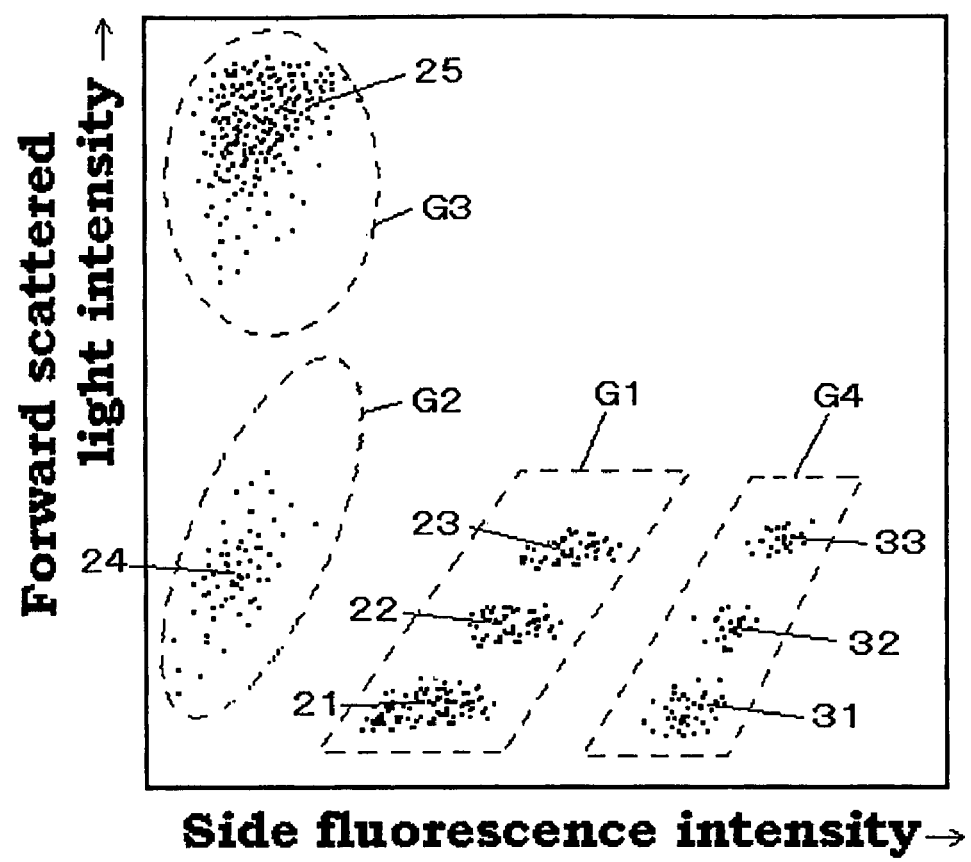
FIG. 4 is a plot illustrating first carrier particles and second carrier particles that emerged at different locations on the two dimensional scattergram.

FIG. 4 shows an example of the two dimensional scattergram when the immunoassays are simultaneously carried out for two parameters. The second carrier particles emerge containing a higher concentration of the fluorescent dye than the carrier particles that emerge at the area G1 (first particles). As with the first carrier particles, the second carrier particles emerge segregated into separate populations depending on the pattern of agglutination, such as unagglutinated single particles 31, agglutinated double particles which occur by agglutinating two carrier particles 32, and agglutinated triple particles 33 which occur by agglutinating three carrier particles. The immunoassay can be carried out for the first and second parameters, respectively, by obtaining the rate of agglutination from the particle size distribution in each area, for example, in the area G1 including the first carrier particles and the area G4 including the second carrier particles.

A display unit such as a CRT, an LCD, and a printer are included at the output portion 14. The results of the immunoassay and the various blood cell counts calculated at the analyzing portion 13, and the two dimensional scattergrams and histograms made upon analysis are output at the output portion 14.

Hereinafter, experiments are illustrated in which blood cell counting and immunoassay (e.g., detection of HBs antigen in whole blood) are carried out by detecting the forward scattered light intensity and the side fluorescence intensity from samples containing blood cells and carrier particles and then analyzing the optical information detected.

For the experiments, a dilution series of seven specimens #1 to #7 containing varying concentrations of HBs antigen were prepared and added to human normal whole blood. The concentrations of specimens #1 to #7 are, respectively: 0 U/mL (#1), 1 U/mL (#2), 3 U/mL (#3), 9 U/mL (#4), 27 U/mL (#5), 81 U/mL (#6), and 243 U/mL (#7).

The blood analyzer embodying features of the present invention shown in FIG. 1 was used for the assay. The blood analyzer 1 includes the sample preparing portion 11, the light detecting portion 12, the analyzing portion 13, and the output portion 14. The sample preparing portion 11 includes a specimen supplying portion 11a, a latex reagent supplying portion 11b, a buffer supplying portion 11c, a diluent supplying portion 11d, a staining solution supplying portion 11e, a first reaction vessel 11f, and a second reaction vessel 11g.

An operator of the blood analyzer 1 sets a latex reagent at the latex reagent supplying portion 11b prior to operating the analyzer. The latex reagent is a reagent containing latex particles of which the surface is sensitized with an antibody or antigen (in this case, anti-HBs antibody), which performs an antigen antibody reaction specific to a substance to be immunoassayed. This latex particle acts as the carrier particle.

The following examples and representative procedures illustrate features in accordance with the present invention, and are provided solely by way of illustration. They are not intended to limit the scope of the appended claims or their equivalents.

Latex Particle Preparation Method

A fluorescent latex particle with particle diameter of 0.78 μm was used as the carrier particle. The surface of the carrier particle is sulfate and contains 1% (w/v) red fluorescent dye (capable of being excited with a laser beam with a wavelength of 633 nm). First, 50 μl of 10% fluorescent latex particle suspension (w/v) was added to 950 μl of a GTA buffer (0.53 mg/mL of 3,3-dimethyl glutaric acid, 0.4 mg/mL of Tris, 0.35 mg/mL of 2-amino-2-methyl-1,3-propanediol, pH 4.6) containing 60 μg of an anti-HBs antibody (mouse monoclonal antibody, commercially available article), and left at 20° C. for 2 hours. This was centrifuged at 10000×g for 10 min and a supernatant was discarded. One (1) mL of a GTA buffer containing 1% (w/v) bovine serum albumin (commercially available) was added to a pellet and sonicated to disperse. The procedure from centrifugation through dispersion was repeated several times. Finally, after centrifuging and discarding the supernatant, 1 mL of a GTA buffer (pH 6.2) containing 220 mg/mL of glycerine and 0.3% (w/v) bovine serum albumin was added to the pellet, and sonicated to disperse, thus providing the latex reagent.

The operator of the blood analyzer 1 sets the reaction buffer prepared as follows at the buffer supplying portion 11c prior to operating the analyzer.

Reaction Buffer Preparation Method 1.6 mg/mL of 3,3-dimethyl glutaric acid, 1.1 mg/mL of 2-amino-2-methyl-1, 3-propanediol, 18.18 mg/mL of Tris, 5% (w/v) of bovine serum albumin, and 0.8% (w/v) dextran (commercially available article), pH 6.70, were prepared to provide the reaction buffer for making the assay sample by adding to the specimen.

The operator of the blood analyzer 1 sets RET SEARCH (II) diluent (supplied by Sysmex Corporation) at the diluent supplying portion 11d prior to operating the analyzer. This is for diluting the sample upon staining the blood cells with a staining solution, as described below.

In addition, the operator of the blood analyzer 1 sets RET SEARCH (II) staining solution (supplied by Sysmex Corporation) at the staining solution supplying portion 11e. The RET SEARCH (II) staining solution contains polymethine fluorescent dye capable of staining nucleic acid in the blood cells and being excited with a laser beam at a wavelength of 633 nm. The nucleic acid in the blood cells is fluorescently stained with this dye.

When the operator of the blood analyzer 1 sets a specimen at the specimen supplying portion 11a and puts the blood analyzer 1 into operation, the specimen supplying portion 11a first measures 20 μl of the specimen and delivers it to the first reaction vessel 11f. Next, the buffer supplying portion 11c delivers 160 μl of the reaction buffer to the first reaction vessel 11f, where the specimen and the reaction buffer are blended for 15 seconds. Subsequently, the latex reagent supplying portion 11b delivers 20 μl of the latex reagent to the first reaction vessel 11f, where the specimen, the reaction buffer, and the latex reagent are blended and incubated at 45° C. for 15 min to make a latex reagent mixture sample. Subsequently, 4.5 μl of the latex reagent mixture sample is delivered from the first reaction vessel 11f to the second reaction vessel 11g. Also, the diluent supplying portion 11d delivers 0.8955 mL of the RET SEARCH (II) diluent to the second reaction vessel 11g, where the latex reagent mixture sample is diluted. Then the staining solution supplying portion 11e delivers 18 μl of the RET SEARCH (II) staining solution to the second reaction vessel 11g, where the staining reaction is carried out for about 31 seconds to prepare the assay sample.

Figure 5:
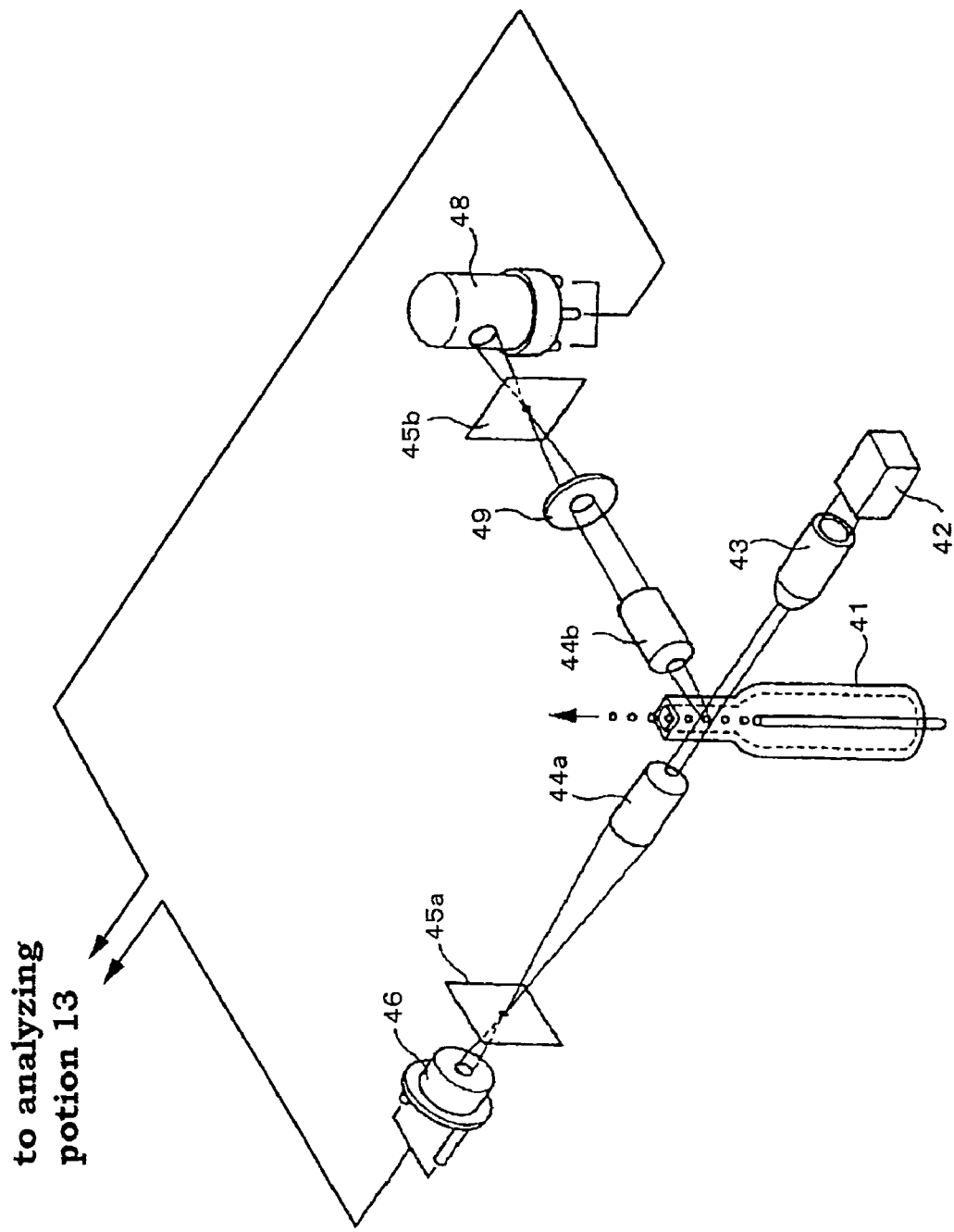
FIG. 5 is a perspective view of a light detecting portion of a blood analyzer embodying features of the present invention.

Then, 2.8 μl of the assay sample prepared in this way is delivered to the light detecting portion 12, and the forward scattered light and side fluorescence are obtained as optical information from each particle contained in the sample. A detailed configuration of the light detecting portion 12 is shown in FIG. 5. The assay sample given pretreatment such as fluorescent staining is flowed into the flow cell 41 (cf., 12a in FIG. 1) to form a sample flow. The laser beam emitted from a semiconductor laser beam source 42 (cf. 12b in FIG. 1) to the sample flow in the flow cell 41 reaches the flow cell 41 through a collimator lens 43, and is emitted to the sample flow. The forward scattered light which occurs when the particle in the sample flow cuts across the laser beam enters the photo diode 46 (cf. 12d in FIG. 1) through a condenser lens 44a and a pin hole 45a. The side fluorescence enters the photo multiplier tube 48 (cf. 12c in FIG. 1) through a condenser lens 44b, a filter 49 and a pin hole 45b. The forward scattered light signal photoelectrically transferred and output at the photo diode 46 and the side fluorescence signal photoelectrically transferred and output at the photo multiplier tube 48 are sent to the analyzing portion 13.

Figure 6:
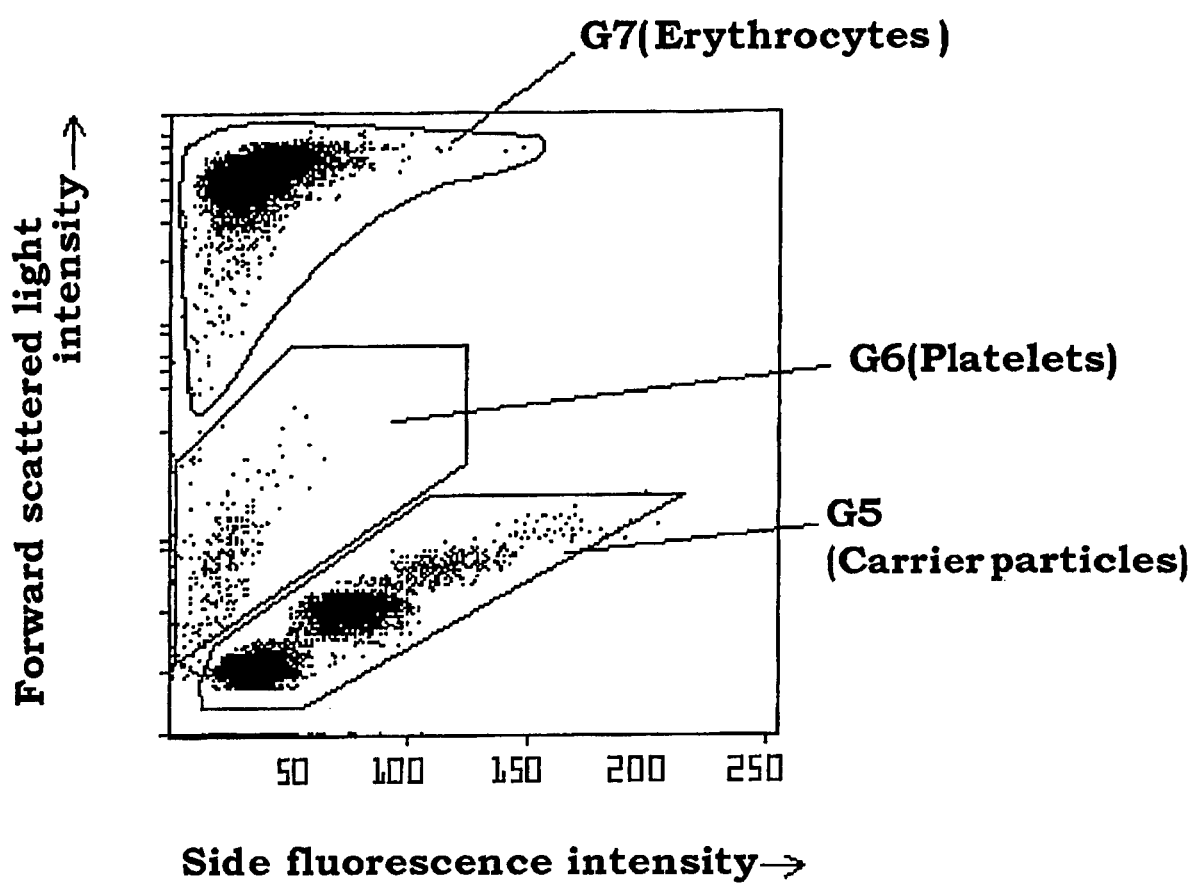
FIG. 6 is a plot showing an example of a two dimensional scattergram.

In the analyzing portion 13, a forward scattered light intensity and a side fluorescence intensity from particle to particle are obtained from the forward scattered light signal and the side fluorescence signal detected at the light detecting portion 12, and a two dimensional scattergram is made using these as parameters. FIG. 6 is the two dimensional scattergram obtained by measuring specimen #6. The vertical and horizontal axes represent the forward scattered light intensity and the side fluorescence intensity, respectively. The platelets, the erythrocytes and the carrier particles form separate populations depending on the differences of the forward scattered light intensity and the side fluorescence intensity. In the two dimensional scattergram in FIG. 6, the area G5 in which the carrier particles are considered to emerge is determined. Similarly, the areas G6 and G7 are determined in which the platelets and the erythrocytes, respectively, are considered to emerge. The determination of the latter area involves the emergence of reticulocytes, which are larger in fluorescent intensity than normal erythrocytes. The emergence area of the erythrocytes G7 includes a location of larger fluorescent intensity than that of mature erythrocytes (i.e., the emergence area of the reticulocytes).

Figure 7:
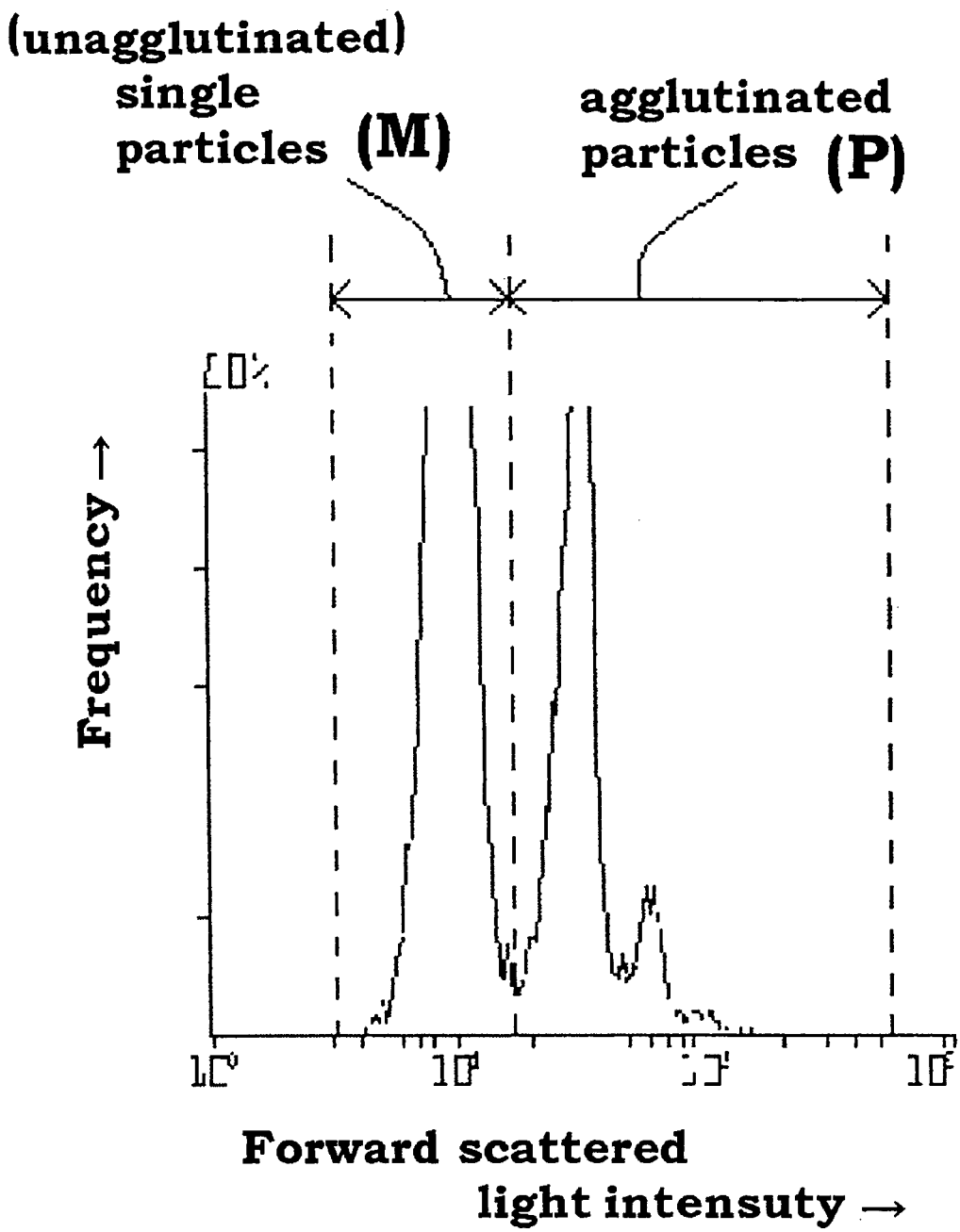
FIG. 7 is a histogram representing particle distribution of particles that emerged in an area of the carrier particles on the two dimensional scattergram.

In FIG. 6, it is found that the carrier particles emerge in the area G5 segregating into single particles, agglutinated double particles, and agglutinated triple particles. The analyzing portion 13 makes a histogram showing the particle size distribution of the particles which emerge in the area G5. FIG. 7 is a histogram showing the particle size distribution of the particles which emerge in the area G5. The vertical and horizontal axes represent the frequency (particle numbers) and the forward scattered light intensity, respectively. The analyzing portion 13 obtains the total particle number T from the single particle number M and the agglutinated particle number P (sum of two or more agglutinated particles) based on the particle size distribution in the area G5 to calculate the rate of agglutination (P/T %). The rates of agglutination of the particles obtained by measuring the specimens #1 to #7 are shown in Table 1.

TABLE 1

| Specimen | Degree of agglutination (P/T %) |
|---|---|
| #1 | 0.37 |
| #2 | 0.78 |
| #3 | 1.80 |
| #4 | 4.91 |
| #5 | 13.46 |
| #6 | 29.68 |
| #7 | 45.31 |

From Table 1 above, it is found that the rates of agglutination vary depending on the anti-HBs antibody concentrations contained in the specimens. Thus, the concentration of the substance to be immunoassayed in a specimen may be obtained by concentration conversion of the rate of agglutination on the basis of a standard curve previously made by measuring the specimens which contain the substance to be immunoassayed at known concentrations.

Figure 8:
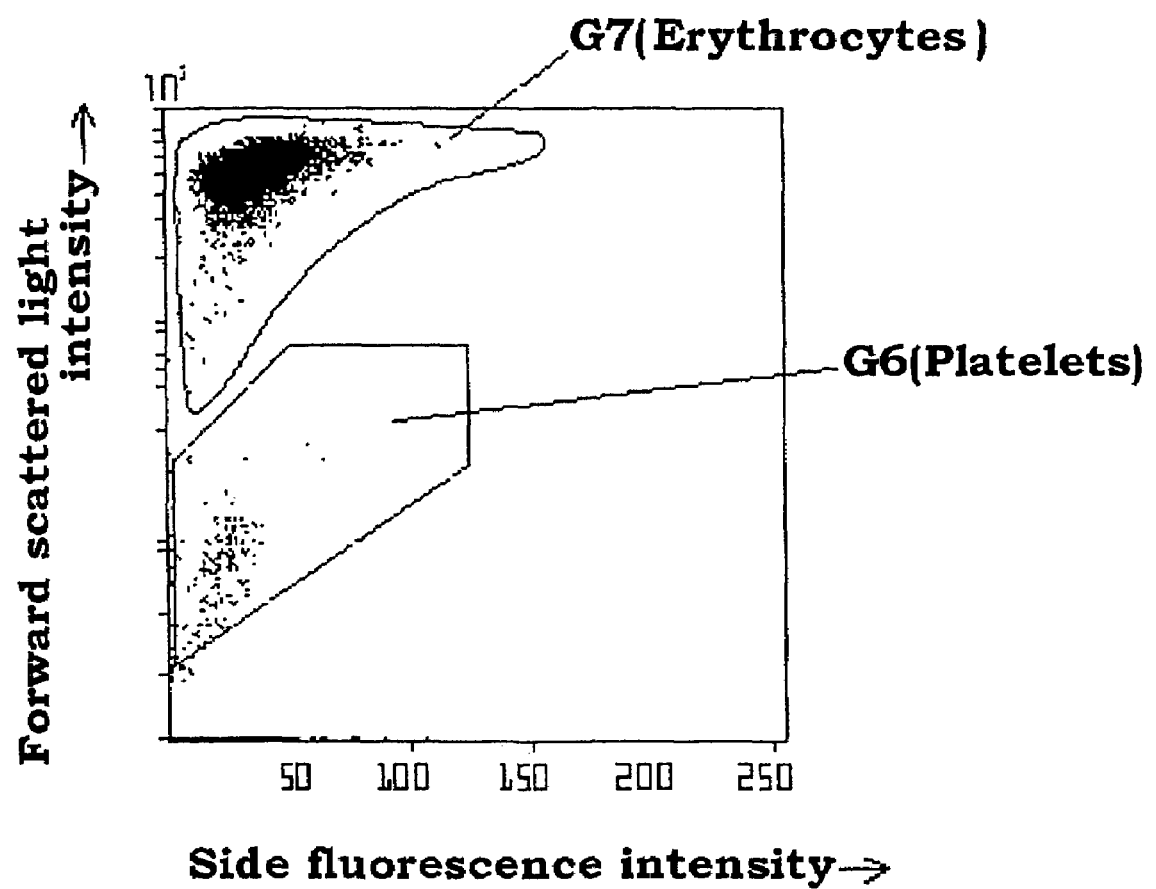
FIG. 8 is a plot showing an example of a two dimensional scattergram.

FIG. 8 shows a two dimensional scattergram obtained by measuring an assay sample prepared using the same human normal whole blood as specimen #1 without adding the latex. The vertical and horizontal axes represent the forward scattered light intensity and the side fluorescence intensity, respectively. Since no latex reagent is contained in the assay sample, no carrier particle emerges on the two dimensional scattergram in FIG. 8 as compared to FIG. 6. There is no difference in the emergence locations for the platelets and the erythrocytes. Thus, it is shown that the presence or absence of the latex reagent does not influence the results of blood cell counting.

Figure 9:
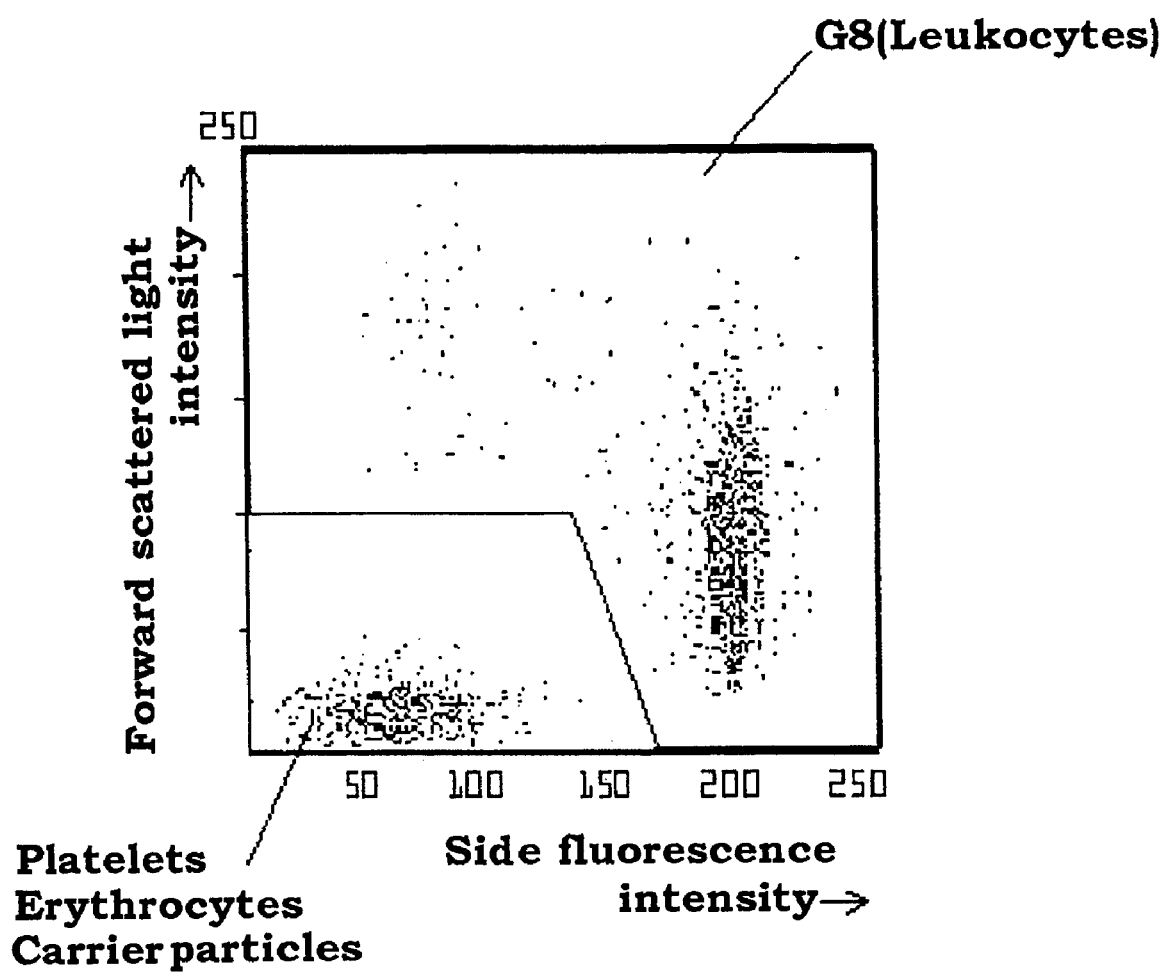
FIG. 9 is a plot showing an example of a two dimensional scattergram.

As described above, on the two dimensional scattergram in FIG. 6, the areas G6 and G7—where the platelets and the erythrocytes, respectively, are considered to emerge—are determined beforehand, and the number of particles which emerge in each area is counted. Among various blood cells, leukocytes are larger in forward scattered light intensity and fluorescence intensity compared to platelets and erythrocytes, and emerge in the location which is not displayed on the two dimensional scattergram shown in FIG. 6 and FIG. 8. Thus, the analyzing portion 13 makes the two dimensional scattergram capable of reflecting the larger forward scattered light intensity and side fluorescence intensity and differentiating the leukocytes from the other particles. Then, the area where the leukocytes are considered to emerge is determined, and the number of particles in the area is counted. The two dimensional scattergram for differentiating and counting the leukocytes is shown in FIG. 9. As with FIG. 6 and FIG. 8, the vertical and horizontal axes represent the forward scattered light intensity and the side fluorescence intensity, but the emergence of leukocytes is identified by extending the display range of the respective parameters. The populations of platelets, erythrocytes, and carrier particles that emerged clearly separate on the two dimensional scattergrams in FIG. 6 and FIG. 8 emerge together at the left bottom and are not displayed as clearly separate on the two dimensional scattergram in FIG. 9. The area G8 is the area where the leukocytes are considered to emerge, and the particles which emerge in this area are subject to counting as leukocytes.

The analyzing portion 13 counts the particles which emerge in the areas G6, G7 and G8 on the two dimensional scattergram to make the platelet number, the erythrocyte number and the leukocyte number, respectively. Also, the volumes of particles counted as erythrocytes are calculated based on forward scattered light intensity and totaled. Then, MCV (mean red cell volume) is calculated by dividing the total value by the particle number.

The specimen #6 was measured by a blood analyzer embodying features of the present invention, and various blood cells were differentiated and counted based on the two dimensional scattergrams in FIG. 6 and FIG. 9. The results were compared with the results in which the same whole blood specimen as in specimen #6 was measured by the conventional method. The conventional method is one in which the entire operation from setting of the whole blood specimen to analysis are performed according to the standard measurement method with an automated hematology analyzer XE-2100 (supplied by Sysmex Corporation). The XE-2100 has a so-called electric resistance detector in addition to an optical detecting system, and the platelet number, the erythrocyte number and MCV (mean red cell volume) are calculated based on the results detected by the electric resistance detector. The leukocyte number is calculated based on the results detected by the optical detecting system.

The measurement results obtained with a blood analyzer embodying features of the present invention and with the conventional method are shown in Table 2 below.

TABLE 2

|  | Present Invention | Conventional Method |
| --- | --- | --- |
| Erythrocytes | 4.70 ($10^6$ cells/µL) | 4.60 ($10^6$ cells/µL) |
| Platelets | 301 ($10^3$ cells/µL) | 302 ($10^3$ cells/µL) |
| Leukocytes | 12.10 ($10^3$ cells/µL) | 12.17 ($10^3$ cells/µL) |
| MCV | 95.8 (fL) | 95.8 (fL) |

As shown in Table 2 above, a good correlation is obtained for respective parameters between the blood cell counting results according to the present invention and the results of the conventional method.

The analyzing portion 13 has a function which performs a hematocrit correction for the results of immunoassay of the whole blood sample. Hereinafter, the hematocrit correction is described.

When a substance to be immunoassayed (e.g., an antibody or an antigen) is present only in serum/plasma, there is a difference in concentration of the substance to be immunoassayed for the case when the immunoassay is performed in the whole blood and the case when the assay is performed in serum or plasma. This difference is due to a difference in volume ratio of the blood cell component that occupies the whole blood (hematocrit value). Since there is an individual difference in hematocrit values, it is difficult to precisely correct the assay value in the case when the assay is performed using the serum or plasma by the method in which the result of the whole blood immunoassay is multiplied by a constant coefficient. Thus, if the so-called hematocrit correction is used when the result of a whole blood immunoassay measured from serum or plasma is corrected, by the use of the hematocrit value obtained from the blood cell counting, the same measurement value as that of the measurement carried out in the serum (or plasma) is obtained.

The hematocrit value is the volume ratio of the blood cell component that occupies the whole blood. An example in which a volume ratio of erythrocytes which occupy a majority of the blood cell component is used as the hematocrit value is described below. In the present analyzer, as above, the volume of each particle counted as the erythrocyte is calculated based on the forward scattered light signal. The volumes of respective particles are totaled, and the MCV is calculated by dividing the sum by the particle number. At the analyzing portion 13, the hematocrit value is calculated by further multiplying this MCV by the particle number. When the concentration of the substance to be immunoassayed in the whole blood is A, the concentration of the substance to be immunoassayed in the serum (or plasma) is B, and the hematocrit value (%) is C, then the concentration B of the substance to be immunoassayed in the serum (or plasma) is obtained from the following formula:

$$B = A \times 100/(100-C)$$

Using this formula, , the concentration at the analyzing portion 13 of the substance to be immunoassayed in the whole blood is converted to the concentration of the substance to be immunoassayed in the serum (or plasma) by performing the correction for a result of the immunoassay in the whole blood using the hematocrit value obtained in the blood cell counting.

At the output portion 14, the results of the immunoassay as well as the calculated results of the hematocrit correction, the various blood cell counts, the two dimensional scattergrams, and the histograms made upon analysis at the analyzing portion 13 are provided.

Figure 10:
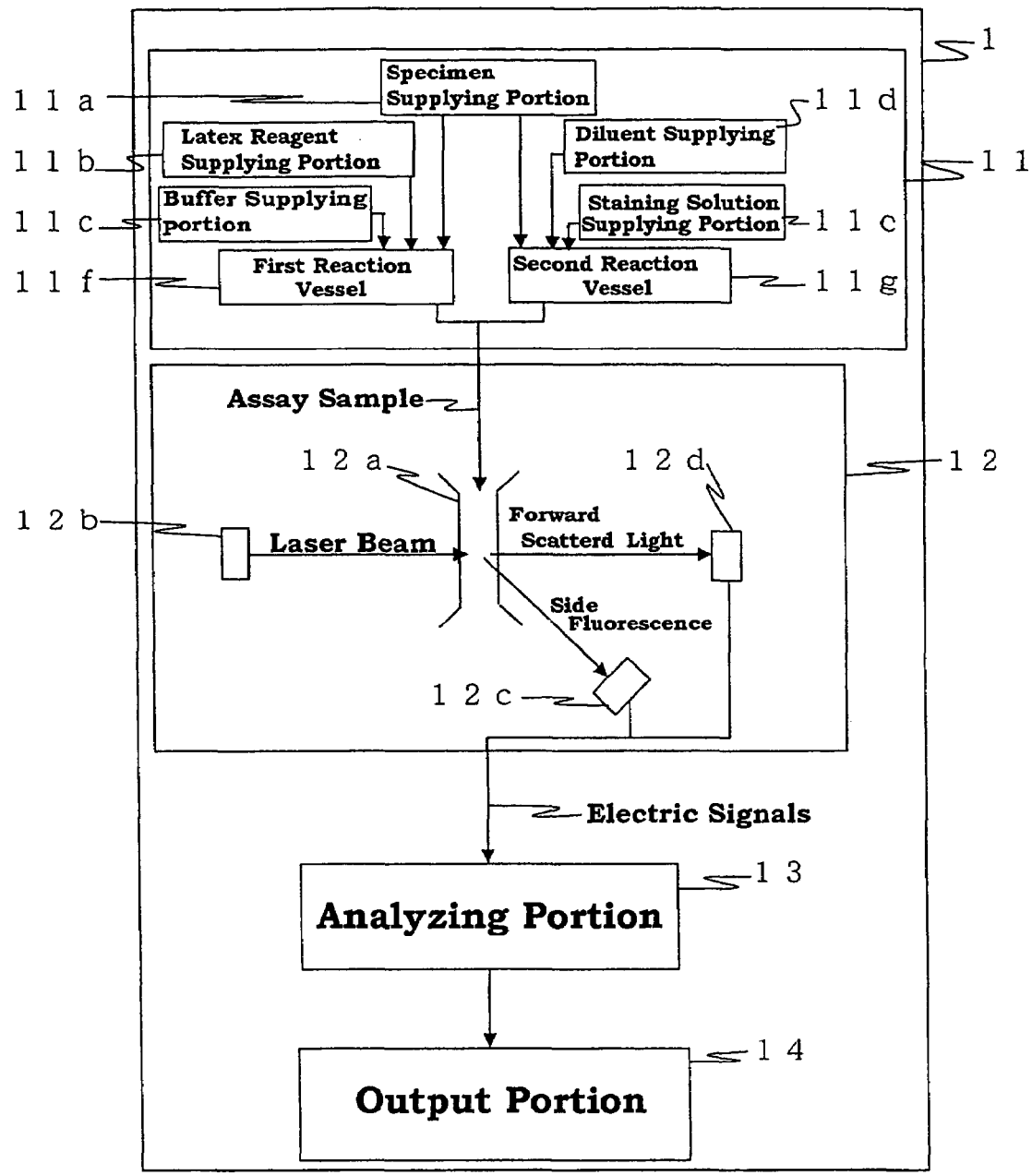
FIG. 10 is a scheme illustrating a second blood analyzer embodying features of the present invention.

FIG. 10 shows an alternative blood analyzer embodying features of the present invention. In this example, the sample preparing portion 11 of the blood analyzer 1 shown in FIG. 1 is made into a configuration to prepare the sample for the immunoassay and the sample for the blood cell counting separately. The same reference numerals are used as in FIG. 1 when the configurations are common.

Hereinafter, the configuration and performance of the blood analyzer 1 shown in FIG. 10 is described. The sample preparing portion 11 includes a specimen supplying portion 11a, a latex reagent supplying portion 11b, a buffer supplying portion 11c, a diluent supplying portion 11d, a staining solution supplying portion 11e, a first reaction vessel 11f, and a second reaction vessel 11g. Prior to operating the blood analyzer 1, an operator sets a specimen at the specimen supplying portion 11a, a reaction buffer at the buffer supplying portion 11c, a diluent at the diluent supplying portion 11d, and a staining solution at the staining solution supplying portion 11e. The specimen, latex reagent, reaction buffer, diluent, and staining solution used are the same as those in the blood analyzer described above.

When the blood analyzer 1 is started, the specimen supplying portion 11a first measures 20 µl of the specimen and delivers it to the first reaction vessel 11f. Next, the buffer supplying portion 11c delivers 160 µl of the reaction buffer to the first reaction vessel 11f, where the specimen and the reaction buffer are blended for 15 seconds. Subsequently, the latex reagent supplying portion 11b delivers 20 μl of the latex reagent to the first reaction vessel 11f, where the specimen/ reaction buffer and the latex reagent are blended and incubated at 45° C. for 15 min to make a sample for the immunoassay.

Subsequently, the specimen supplying portion 11a measures 20 μL of the specimen and delivers it to the second reaction vessel 11g. The diluent supplying portion 11d delivers 0.8955 mL of the RET SEARCH (II) diluent to the second reaction vessel 11g to dilute the specimen. Next, the staining solution supplying portion 11e delivers 18 μl of the RET SEARCH (II) staining solution to the second reaction vessel 11g, where the staining reaction is carried out for about 31 seconds to prepare a sample for the blood cell counting.

Subsequently, the sample for immunoassay in the first reaction vessel 11f is delivered to a flow cell 12a of a light detecting portion 12, and the side fluorescence signal and the forward scattered light signal are detected from each particle in the sample. Next, the sample for blood cell counting in the second reaction vessel 11g is delivered to the flow cell 12a of the light detecting portion 12, and the side fluorescence signal and the forward scattered light signal are detected from each particle in the sample. The detected signals are sent to an analyzing portion 13. Thus, the sample for immunoassay and the sample for blood cell counting are delivered to the same flow cells, respectively, and their optical information is detected. The performance of the light detecting portion 12 upon the detection of optical information from respective samples is analogous to the case of the blood analyzer described in FIG. 1 above.

Figure 11:
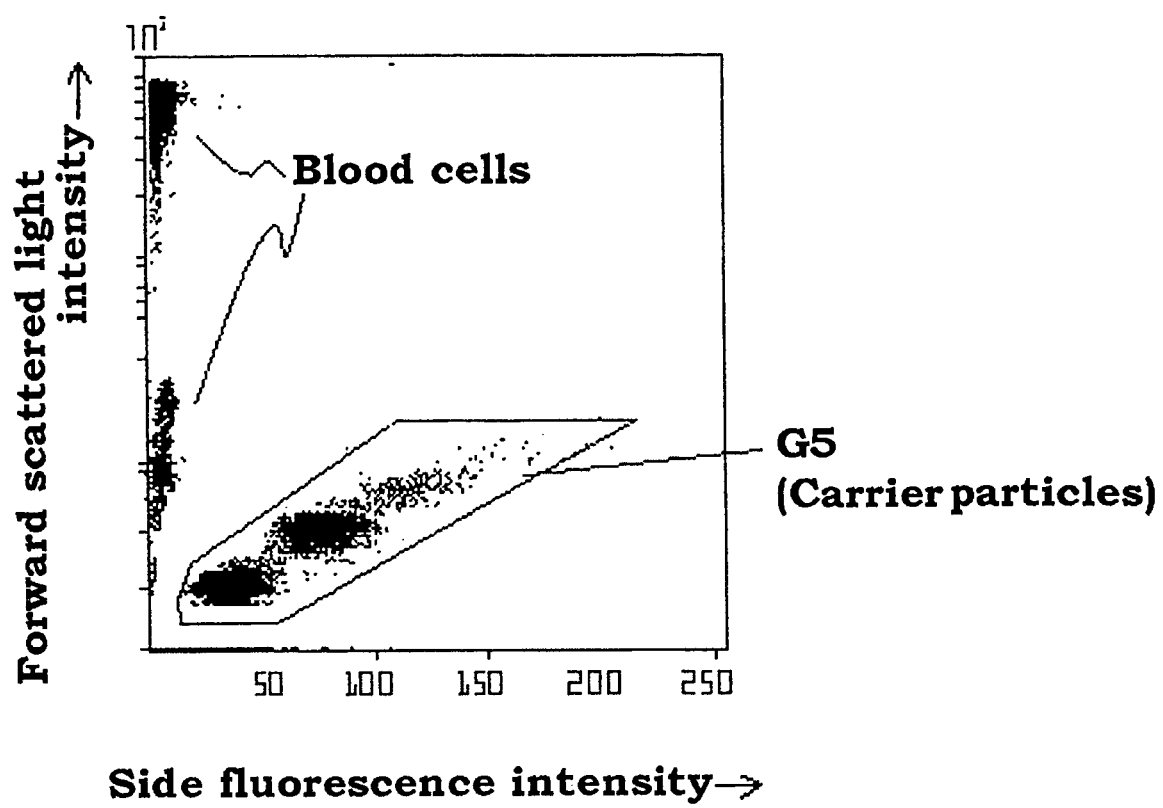
FIG. 11 is a plot showing an example of the two dimensional scattergram.

The analyzing portion 13 makes a two dimensional scatter gram based on the side fluorescence signal and the forward scattered light signal detected from the sample for immunoassay. An example of the two dimensional scattergram is shown in FIG. 11. Since the staining solution for fluorescently staining the blood cells is not added to this sample for immunoassay, only carrier particles have strong fluorescent intensity among the particles involved in the sample. Thus, S/N ratio is improved when the carrier particles are differentiated from the particles involved in the sample. Differentiating of the carrier particles and the calculation of rate of agglutination are carried out analogous to the case of the blood analyzer described in reference to FIG. 1 above. Then, the concentration of the substance to be immunoassayed is obtained by concentration conversion on the basis of a standard curve.

Figure 12:
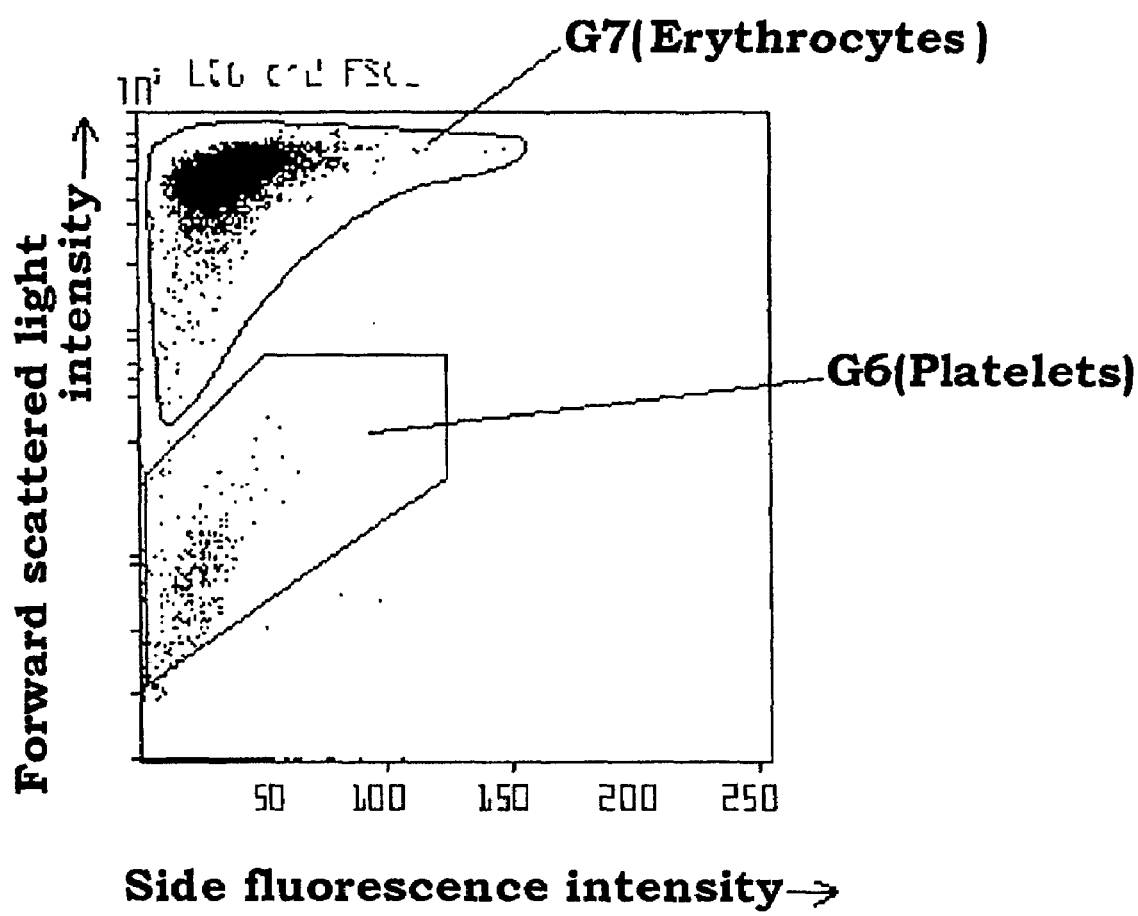
FIG. 12 is a plot showing an example of the two dimensional scattergram.
Figure 13:
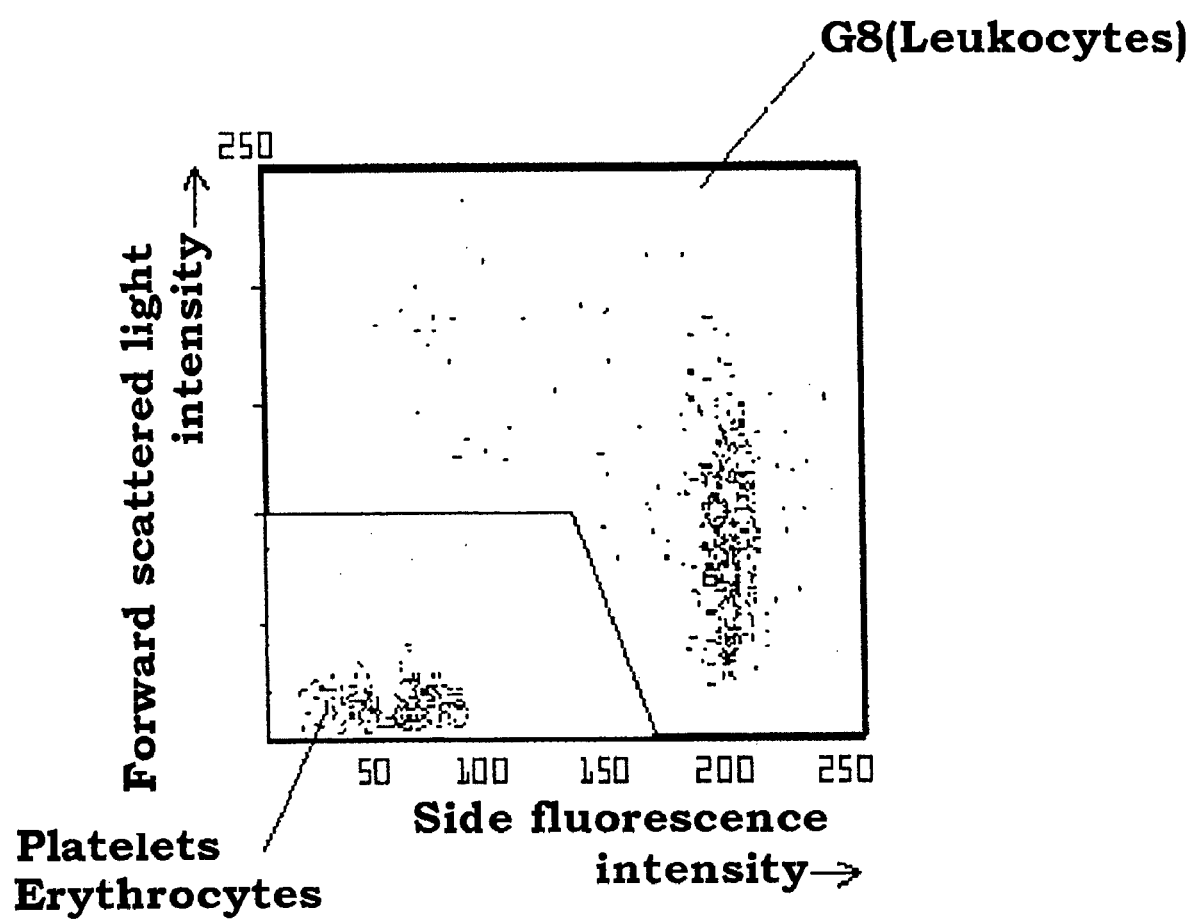
FIG. 13 is a plot showing an example of the two dimensional scattergram.

Also, the analyzing portion 13 makes the two dimensional scattergram based on the side fluorescence signal and the forward scattered light signal detected from the sample for blood cell counting. Examples of the two dimensional scattergrams obtained from the sample for blood cell counting are shown in FIG. 12 and FIG. 13. FIG. 12 and FIG. 13 correspond to FIG. 6 and FIG. 9, respectively. Since the carrier particles for the immunoassay are not added to this sample for blood cell counting, only blood cells emerge on the two dimensional scattergram. Then, as is the case with the blood analyzer described in reference to FIG. 1 above, the blood cells are differentiated into erythrocytes, leukocytes and platelets based on the areas determined beforehand on the two dimensional scattergram, and then counted.

The results of immunoassay and blood cell counting in the analyzing portion 13 are output at the output portion 14. As is the case with the blood analyzer shown in FIG. 1, the hematocrit value may be calculated based on the result of blood cell counting. In alternative embodiments, the result of immunoassay may be corrected based on that hematocrit value.

As described above, even if the sample for immunoassay and the sample for blood cell counting are separately prepared and the detection of optical information at the light detecting portion 12 is separately performed, the light detecting portion 12 can be utilized in common with the immunoassay and blood cell counting.

In the presently preferred embodiments of the invention described above, the forward scattered light and the side fluorescence were used as the optical information detected from the samples for blood cell counting and immunoassay. However, the optical information is not limited thereto, and those commonly obtained from the blood cells and carrier particles can be selected from optical information such as side fluorescence, absorbance, phosphorescence, chemiluminescence, and bioluminescence. Also, various dyes or luminescent substrates can be contained in the carrier particles depending on the optical information used.

Physical properties other than optical information that reflect characteristics of the particles may be detected from each particle and differentiating of respective particles may be carried out based on the physical property. For example, using a physical property wherein electrodes are disposed to sandwich an orifice as a detector in a state of applied voltage between the electrodes, a particle to be assayed is passed through the orifice. When the particle passes through the orifice, electric resistance takes place in proportion to the particle size. Thus, the level of this electric resistance can be detected as the physical property which each particle has. As the detector for measuring the particle by utilizing the electric resistance in this way, it is possible to use, for example, those described in U.S. Pat. No. 5,905,214.

When differentiating of the cells is performed based on the levels of electric resistance detected from respective particles, it is preferred that the particle diameter and electric resistance of the carrier particles are controlled so as to discriminate the blood cells and carrier particles.

In accordance with the present invention, it becomes possible for the blood cell counting and immunoassay to be carried out using the identical measurement section (the light detecting portion in the embodiment described above). In addition, the specimens and reagents may be commonly used over multiple assay parameters. Furthermore, in the immunoassay, the present invention enables whole blood assay without the need for centrifugation and can shorten the time period from specimen collection to the obtainment of the test result. Since the hematocrit correction performed for the results of immunoassay can be carried out based on blood cell counting obtained from the same blood sample, the hematocrit correction can be carried out more precisely.

The foregoing detailed description and accompanying drawings have been provided by way of explanation and illustration, and are not intended to limit the scope of the appended claims. Many variations in the presently preferred embodiments illustrated herein will be obvious to one of ordinary skill in the art, and remain within the scope of the appended claims and their equivalents.

What is claimed is:

1. An analyzer comprising:
 a sample preparing portion configured for preparing an assay sample comprising a reagent and a whole blood specimen, the sample preparing portion comprising:
  a reaction vessel and a reagent supplying portion for supplying the reagent to the reaction vessel, wherein the reagent comprises fluorescent carrier particles sensitized with an antibody or an antigen against a target substance found in the serum or blood plasma portion of the whole blood specimen;

a flow cell;
an assay sample supplier for supplying the assay sample from the reaction vessel to the flow cell;
a light source for irradiating the assay sample in the flow cell;
a first detector that detects fluorescence intensities from irradiated particle components including blood cells and fluorescent carrier particles that reacted to the target substance in the assay sample;
a second detector that detects scattered light intensities from irradiated particle components including blood cells and fluorescent carrier particles that reacted to the target substance in the assay sample; and
an analyzing portion device configured:
  differentiate the blood cells and the fluorescent carrier particles based on the detected fluorescence intensities received from the first detector and the detected scattered light intensities received from the second detector;
  count the differentiated blood cells; and
  differentially detect agglutination degree of the fluorescent carrier particles that reacted to the target substance.

2. The blood analyzer of claim 1, further comprising a second reagent supplying portion for supplying the reagent to the reaction vessel, wherein the assay sample further comprises a second reagent comprising a fluorescent dye for staining blood cells.

3. The blood analyzer of claim 2 wherein the analyzing portion differentiates blood cells into erythrocytes, leukocytes, and platelets, and wherein the analyzing portion counts the differentiated blood cells.

4. The blood analyzer of claim 1, wherein the operations further comprise:
  obtaining a concentration value of the target substance based on the detected agglutination degree; and
  correcting the concentration value as a whole blood immunoassay result to a concentration value as a serum or plasma immunoassay result based on a result of blood cell counting.

5. The blood analyzer of claim 1, wherein the operations further comprise: obtaining a concentration value of the target substance based on the detected agglutination degree;
  obtaining a hematocrit value based on size information of blood cells; and
  correcting the concentration value as a whole blood immunoassay result to a concentration value as a serum or plasma immunoassay result based on the hematocrit value.

6. An analyzer comprising:
a sample preparing portion configured for preparing an immunoassay sample for an immunoassay by adding a first reagent for the immunoassay to a first specimen split from a whole blood specimen, and for preparing a counting sample for blood cell counting by adding a second reagent for the blood cell counting to a second specimen split from the whole blood specimen;
  wherein the first reagent comprises fluorescent carrier particles sensitized with an antibody or an antigen against a target substance found in the serum or blood plasma portion of the whole blood specimen;
  wherein the second reagent comprises a fluorescent dye for staining blood cells; and
  wherein the sample preparing portion comprises a first reaction vessel for preparing the immunoassay sample, a second reaction vessel for preparing the counting sample, a first reagent supplying portion for supplying the first reagent to the first reaction vessel, and a second reagent supplying portion for supplying the second reagent to the second reaction vessel;
a flow cell;
an immunoassay sample supplier for supplying the immunoassay sample from the first reaction vessel to the flow cell;
a counting sample supplier for supplying the counting sample from the second reaction vessel to the flow cell;
a light source for irradiating the immunoassay sample or the counting sample in the flow cell;
a first detector that detects fluorescence intensities from irradiated particle components including fluorescent carrier particles that reacted to the target substance contained in each of the immunoassay sample and the counting sample;
a second detector that detects scattered light intensities from irradiated particle components including fluorescent carrier particles that reacted to the target substance contained in each of the immunoassay sample and the counting sample; and
an analyzing portion device configured to:
  differentiate the fluorescent carrier particles from the blood cells based on the detected fluorescence intensities of the immunoassay sample by the first detector and the detected scattered light intensities transmitted by the second detector;
  differentially detect agglutination degree of the fluorescent carrier particles that reacted to the target substance;
  differentiate the blood cells based on the detected fluorescence intensities of the count sample transmitted by the first detector and the detected scattered light intensities of the counting sample transmitted by the second detector; and
  counting the differentiated blood cells.

7. The blood analyzer of claim 6, wherein the analyzing portion differentiates blood cells into erythrocytes, leukocytes, and platelets, and wherein the analyzing portion counts the differentiated blood cells.

8. The blood analyzer of claim 6, wherein the operations further comprise:
  obtaining a concentration value of the target substance based on the detected agglutination degree; and
  correcting the concentration value as a whole blood immunoassay result to a concentration value as a serum or plasma immunoassay result based on a result of blood cell counting.

9. The blood analyzer of claim 6, wherein the operations further comprise:
  obtaining a concentration value of the target substance based on the detected agglutination degree;
  obtaining a hematocrit value based on size information of blood cells; and
  correcting the concentration value as the whole blood immunoassay result to a concentration value as a serum or plasma immunoassay result based on the hematocrit value.

10. An analyzer comprising:
a sample preparing portion configured for preparing an assay sample comprising a reagent and a whole blood specimen, the sample preparing portion comprising:
  a reaction vessel and a reagent supplying portion for supplying the reagent to the reaction vessel, wherein the reagent comprises fluorescent carrier particles sensitized with an antibody or an antigen against a target substance found in the serum or blood plasma portion of the whole blood specimen;

a flow cell;

an assay sample supplier for supplying the assay sample from the reaction vessel to the flow cell;

a light source for irradiating the assay sample in the flow cell;

a first detector that detects fluorescence intensities from irradiated particle components including blood cells and fluorescent carrier particles that reacted to the target substance in the assay sample through a first device that converts a first non-electrical energy into first electrical energy;

a second detector that detects scattered light intensities from irradiated particle components including blood cells and fluorescent carrier particles that reacted to the target substance in the assay sample through a second device that converts a second non-electrical energy into second electrical energy; and an analyzing system comprising:

a differentiating processor that differentiates blood cells and the fluorescent carrier particles that reacted to the target substance by processing output transmitted by the first detector and the second detector;

a measuring detector that counts the differentiated blood cells; and an agglutination processor in communication with the second detector that differentially detects agglutination degree of the fluorescent carrier particles that reacted to the target substance.

11. The analyzer of claim 10 further comprising a visual output device in communication with the agglutination processor to display physical agglutination patterns.

12. The analyzer of claim 10 where the agglutination processor comprises means for detecting agglutination degree of the fluorescence carrier particles based on the detected scattered light intensities captured in the output of the second detector.

* * * * *

UNITED STATES PATENT AND TRADEMARK OFFICE
CERTIFICATE OF CORRECTION

PATENT NO. : 7,618,587 B2
APPLICATION NO. : 10/629296
DATED : November 17, 2009
INVENTOR(S) : Yasunori Kawate It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1096 days.

Signed and Sealed this

Twenty-sixth Day of October, 2010

David J. Kappos
*Director of the United States Patent and Trademark Office*